United States Patent
Carredano et al.

(10) Patent No.: US 10,376,813 B2
(45) Date of Patent: Aug. 13, 2019

(54) DETERMINATION OF CHROMATOGRAPHY CONDITIONS

(71) Applicant: GE Healthcare Bio-Sciences AB, Uppsala (SE)

(72) Inventors: Enrique Napoleon Carredano, Uppsala (SE); Gustav Jose Rodrigo, Uppsala (SE)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 175 days.

(21) Appl. No.: 15/173,215

(22) Filed: Jun. 3, 2016

(65) Prior Publication Data
US 2016/0367911 A1    Dec. 22, 2016

(30) Foreign Application Priority Data
Jun. 16, 2015    (GB) .................................. 1510477.1

(51) Int. Cl.
| | | |
|---|---|---|
| *B01D 15/36* | (2006.01) | |
| *B01D 15/16* | (2006.01) | |
| *B01D 15/34* | (2006.01) | |
| *B01D 15/42* | (2006.01) | |

(52) U.S. Cl.
CPC ......... *B01D 15/362* (2013.01); *B01D 15/166* (2013.01); *B01D 15/34* (2013.01); *B01D 15/424* (2013.01)

(58) Field of Classification Search
CPC .... B01D 15/362; B01D 15/424; B01D 15/34; B01D 15/166
See application file for complete search history.

(56) References Cited

U.S. PATENT DOCUMENTS

| | | | | |
|---|---|---|---|---|
| 9,017,687 | B1* | 4/2015 | Wang ................... | C07K 16/241 424/158.1 |
| 2009/0098660 | A1* | 4/2009 | Falkenstein .......... | B01D 15/362 436/501 |
| 2011/0039712 | A1* | 2/2011 | Bjorkesten ............. | B01D 15/12 506/7 |
| 2012/0022239 | A1* | 1/2012 | Van Alstine ..... | A61K 39/39591 530/388.1 |
| 2012/0043208 | A1* | 2/2012 | Jin ................... | G01N 27/44756 204/452 |
| 2013/0041139 | A1* | 2/2013 | Brown ..................... | C07K 1/22 530/388.1 |
| 2013/0218352 | A1* | 8/2013 | Iovanni ................ | G05D 7/0617 700/282 |
| 2013/0338344 | A1* | 12/2013 | Ramasubramanyan | ..................... C07K 1/165 530/389.2 |

(Continued)

OTHER PUBLICATIONS

GE , Inline conditioning for process chromatography systems, 2010.*

(Continued)

*Primary Examiner* — Mohammad K Islam
(74) *Attorney, Agent, or Firm* — Wood IP LLC

(57) ABSTRACT

The present invention relates to a method for the determination of chromatography conditions for the separation of a biomolecule from a liquid sample, which method comprises selecting a number of experiments using design of experiments (DoE); performing said experiments with in-line conditioning of orthogonal quality measures; and based on the results from the experiments, determining efficient chromatography conditions for said biomolecule.
The invention also relates to a system for performing the method as well as a computer program and an instrument comprising such a computer program.

20 Claims, 2 Drawing Sheets

(56) References Cited

U.S. PATENT DOCUMENTS

| | | | |
|---|---|---|---|
| 2014/0288278 A1* | 9/2014 | Nti-gyabaah | B01D 15/3809 530/388.24 |
| 2014/0301977 A1* | 10/2014 | Nadarajah | B01D 15/14 424/85.2 |
| 2015/0110799 A1* | 4/2015 | Ramasubramanyan | C07K 16/241 424/142.1 |
| 2015/0285771 A1* | 10/2015 | Wang | C07K 1/18 436/501 |
| 2016/0161455 A1* | 6/2016 | McDonald | B01D 15/362 506/9 |
| 2017/0058019 A1* | 3/2017 | Felfoldi | C07K 1/18 |
| 2017/0157566 A1* | 6/2017 | Gefroh | B01D 61/142 |

OTHER PUBLICATIONS

Training (Multivariate Data Analysis (MVA) and Design of Experiments (DoE)—Chemometrics & Spectroscopic Applications, 2010.*

GE, Inline conditioning for process chromatography systems (Year: 2010).*

Training (Multivariate Data Analysis (MVA) and Design of Experiments (DoE)—Chemometrics & Spectroscopic Applications (Year: 2010).*

GB Search Report regarding GB Application No. 1510477.1, dated Feb. 26, 2016, 3 pages.

Paul et al., Journal of Chromatography A, vol. 1366, 2014, "Optimization of a preparative multimodal ion exchange step for purification of a potential malaria vaccine", pp. 38-44.

Rafamantanana et al., Journal of Pharmaceutical and Biomedical Analysis, vol. 62, 2012, "Application of design of experiments and design space methodology for the HPLC-UV separation optimization of aporphine alkaloids from leaves of Spirospermum penduliform Thouars", pp. 23-32.

Fekete et al., Journal of Pharmaceutical and Biomedical Analysis, vol. 115, 2015, "Ion-exchange chromatography for the characterization of biopharmaceuticals", pp. 43-55.

* cited by examiner

DETERMINATION OF CHROMATOGRAPHY CONDITIONS

CROSS-REFERENCE TO RELATED APPLICATIONS

This application claims priority to GB application number 1510477.1, filed Jun. 16, 2015, the entire disclosure of which is hereby incorporated by reference.

TECHNICAL FIELD

The present invention relates to the field of bioprocessing, and more specifically to the optimization of conditions used to purify or separate one or more biomolecules from a liquid. Thus, the present invention relates to a method for determining chromatography conditions specific for a selected biomolecule as well as to a system for performing the method.

BACKGROUND

The area known as bioprocessing relates to the characterization, expression and purification of biomolecules. In the purification of biomolecules, chromatography is still used as at least one step in almost all processes approved by the authorities for the manufacture of a biomolecule, such as a drug or a vaccine. A common feature for all the different principles of chromatography, such as affinity chromatography, ion exchange chromatography, hydrophobic interaction chromatography and multimode chromatography is that a number of operating variables—or quality measures—are available to design and optimise efficient processing.

Design of Experiments (DoE) is a commonly applied technique for planning and analyzing experiments, allowing the use of a minimum number of experiments, in which you can systematically vary several experimental parameters simultaneously and capturing as much information as possible. In general usage, design of experiments (DoE) or experimental design is the design of any information-gathering exercises where variation is present, whether under the full control of the experimenter or not. In the design of experiments, the experimenter is often interested in the effect of some process or intervention on some objects. Design of experiments is thus a discipline that has very broad application across all the natural and social sciences and engineering, but which has proved suitable to apply in bioprocessing.

Commercial products are available for using DoE in the optimization of chromatography conditions. For example, the AKTA™ avant 25 system (GE Healthcare, www.gelifesciences.com) has been used with the Design of Experiments (DoE) functionality of the UNICORN™ 6 control software (GE Healthcare, www.gelifesciences.com) to perform a DoE of loading and elution conditions resulting in a strategy for process development and scale-up of a recombinant protein purification (GE Healthcare, www.gelifesciences.com, Application Note 28-9827-80 AA). Even if the DoE helps reducing the number of experiments, with this approach one will still need to do experiments representative for the full range of each variable, resulting in a relatively large number of experiments, which of course require time and resource.

PreDictor RoboColumn™ units, which are commercially available prepacked, miniaturized columns that support high throughput process development (HTPD) may be used for DoE with a robotic liquid handling workstation, such as Freedom Evo™ (Tecan) for parallel chromatographic separations. Up to eight different conditions may be tested. However, as a pressure fall may appear when the needle of the robot leaves the column to re-fill liquid, the flow rate may not be totally constant. As the volumes of collected fractions are unknown, they will have to be determined experimentally.

EP 2 269 055 (Björkesten et al: "Preparation of liquid mixtures") relates to a method of generating a liquid mixture of controlled pH and ionic strength, as well as to an apparatus applicable in such a method. One aspect of EP 2 269 055 is to provide a method of precise and accurate control of the pH and ionic strength of a liquid mixture. In brief, this may be achieved by providing a method of preparing a liquid mixture, such as a buffer, which method takes into account both the size and charge of organic as well as inorganic ions. A further object of EP 2 269 055 is to provide an improved method of buffer preparation, wherein the exact composition is first calculated and the buffer is subsequently prepared in a single step. A specific aspect of EP 2 269 055 is to provide the tools for buffer preparation wherein there is a guaranteed pH range for each respective buffer by calculation of the buffer capacity.

However, there is still a need in the bioprocessing area of faster ways of optimizing the conditions for separation of a selected biomolecule from a complex solution, such as antibodies from a liquid originating directly from a liquid cell culture, or from upstream processing of a liquid cell culture.

SUMMARY OF THE INVENTION

One object of the present invention is to provide for efficient purification or separation of a target biomolecule from a liquid sample comprising undesired compounds, molecules or species, such as contaminants and/or impurities, wherein optimized conditions may be predicted based on few chromatographic runs.

Thus, a first aspect of the present invention is a method for determination of chromatography conditions for the separation of a biomolecule from a liquid sample, which method comprises selecting a number of experiments using design of experiments (DoE); performing said experiments with in-line conditioning of at least two gradients of two selected quality measures; and based on the results from said experiments, determining efficient chromatography conditions for said biomolecule; wherein the experiments selected use orthogonal quality measures.

Another object of the invention is to provide for equipment such as software and instrumentation for the optimization of chromatography conditions for biomolecules.

Thus, a second aspect of the invention is a system for the determination of chromatography conditions for the separation of a biomolecule from a liquid sample, which system comprises means for selecting a number of experiments including at least two gradients of two selected quality measures; and means for outputting to a controller for carrying out the experiments;

wherein the experiments selected use orthogonal quality measures and the selected experiments include in-line conditioning of buffer gradient(s).

Other embodiments and advantages of the present invention will appear from the dependent claims as well as from the detailed description provided below.

DEFINITIONS

Figure 1:
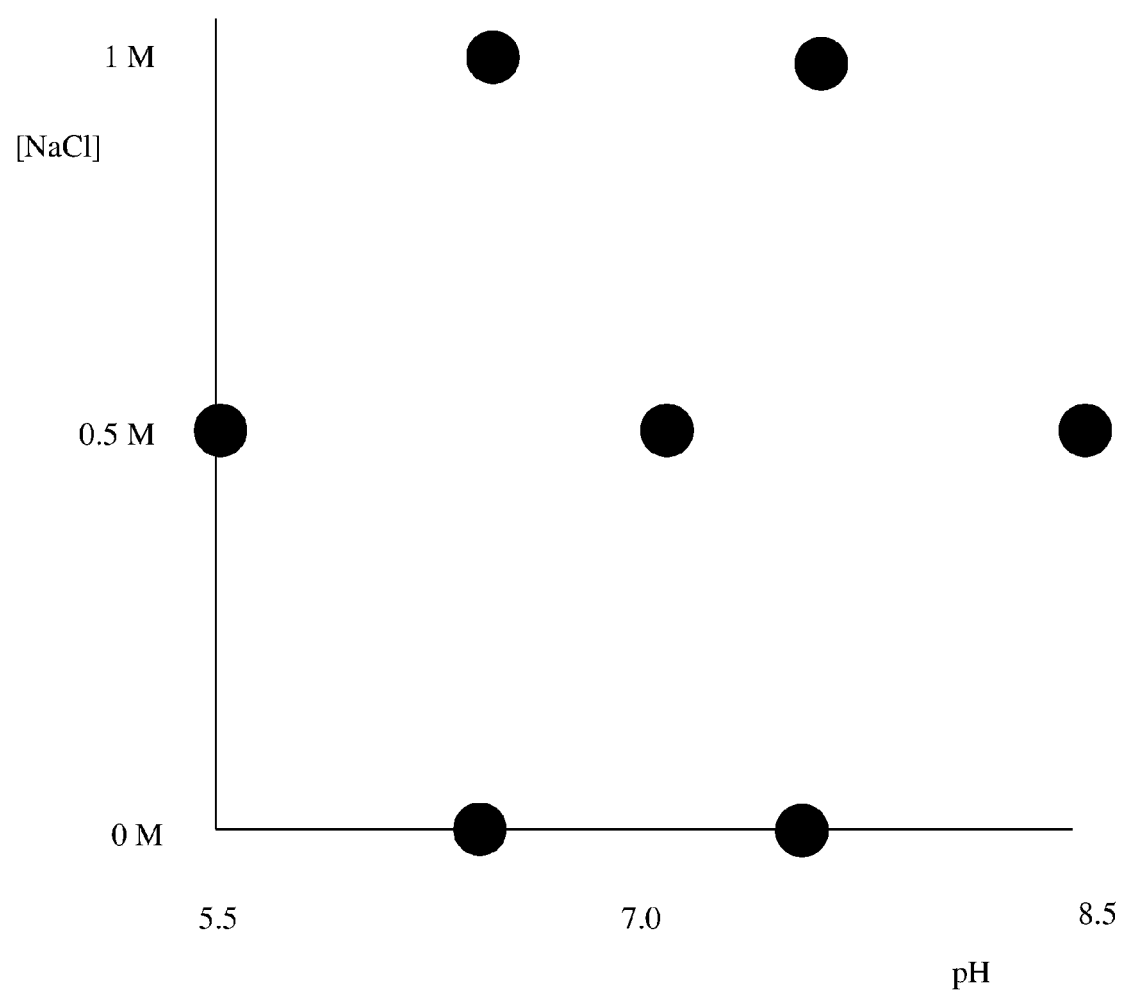
FIG. 1 shows traditional DoE, in accordance with the prior art, with isocratic elution.

The term "biomolecule" is used herein in its broad and conventional meaning of an organic molecule, including a macromolecule such as a protein, peptide or nucleic acid.

The term "chromatography" as used herein includes all methods based on separation and/or isolation of one or more targets from a liquid using its interactions with an inert phase.

The term "Design of Experiments" as used herein means an experimental setup where one or more process variables are deliberately changed in order to observe the effect of the changes on one or more response variables.

The term "surface determinant" as used herein is the part of a biomolecule which is recognizable e.g. by the functional groups of a chromatography resin, such as affinity ligands, charged ligands or the like. A surface determinant may be conformational, i.e. based on structure or linear. A typical surface determinant of a protein is known as an epitope.

The term "quality measure" as used herein means a process variable. Examples of quality measures are for example separation principles, such as ion exchange or hydrophobic interaction chromatography; and properties of the liquid sample such as pH or ionic strength.

The term "orthogonal" in this context is used for independent or different quality measures, i.e. quality measures not related to each other, which affect the chromatographic purification step, such as pH and conductivity.

The term "gradient" as used herein means a change of properties in the mobile phase during a chromatography sample run.

The term "isocratic" as used herein means that the composition of the mobile phase remains constant throughout the chromatography sample run.

The term "binding buffer" is used herein interchangeable with "loading buffer" and means the liquid in which the biomolecule is present as it is applied to a chromatography media.

The term "chromatography resin" is used herein for the inert or solid phase used in chromatography which may or may not include functionalized groups. Such "resin" is sometimes denoted "media" or a "matrix" in the area of chromatography.

DETAILED DESCRIPTION OF THE INVENTION

In the first aspect, the present invention relates to a method for determination of chromatographic conditions for the separation of a biomolecule from a liquid sample, which method comprises selecting a number of experiments using design of experiments (DoE); performing said experiments with in-line conditioning of at least two gradients of two selected quality measures; and, based on the results from said experiments, determining efficient chromatography conditions for said biomolecule; wherein the experiments selected use at least one quality measure.

The skilled person in this field is familiar with the basic concepts of design of experiments (DoE), which is a procedure for planning and predicting experiments so that the data obtained can be analysed using few experiments while still obtaining valid and objective conclusions. Thus, in the present method, the chromatograms, or data, resulting from performing the selected experiments will be fed into an algorithm which calculates efficient conditions for separation of the biomolecule by chromatography. In this context, it is understood that "separation" is a broad term which includes "purification" which is generally known to provide a biomolecule of higher purity. The term "efficient" is understood to mean herein suitable or useful conditions for a predetermined purpose.

In one embodiment, the present method determines the optimal chromatography conditions for a given biomolecule. In this context, "optimal" means the conditions which provide the highest purity of the biomolecule possible.

As the DoE performed according to the present invention will consist of gradients of at least two orthogonal quality measures, an advantage of the invention is the speed by which a separation process may be designed according to the invention. In one embodiment, the experiments are selected using DoE which includes multivariate analysis, a statistical tool which is well known to the skilled person. Methodologies and software for DoE in the bioprocessing area are readily available from commercial sources, as discussed in the section Background above.

The present invention may be used to determine suitable conditions, preferably optimized conditions, for a chromatographic separation such as the suitable or optimal type of chromatography resin; loading volume, wash volume, elution volume, binding buffer; elution buffer; surface determinants of the biomolecule and impurities present in the same liquid sample. The buffer conditions may include pH, buffer strength, acid/base conditions, salt content/ionic strength etc.

More specifically, the few chromatographic experiments required in accordance with the present invention are with advantage increasing or decreasing gradients or constant values of pH and increasing or decreasing gradients or constant values of one among the following buffer properties: Ionic strength, salt concentration, buffer concentration, buffer capacity and conductivity. The gradients may be linear and even curved in shape; either concave or convex. In order to perform the experiments in the DoE in less number of chromatographic runs as compared to the number of experiments in the DoE, the path and curvature of the gradients are designed so that all the points in the DoE are close to the path of the gradients. In order to improve the information content even further, the few chromatographic experiments should be repeated using orthogonal separation principles like ion exchange, hydrophobic interaction chromatography, and/or multimodal ligands. The data can be obtained on line in real time; or it can be obtained off-line from collected fractions in which case the sampling strategy can be setup beforehand with optimal averaging window. In the case of an elution study for instance, at least one fraction should be collected for each of the DoE points passed by. The data obtained are then translated into a series of experimental descriptors of the separation problem. The responses are used to train the DoE regression model which then is used to predict the optimal isocratic conditions. Alternatively a qualitative assessment of the elution map may be used to obtain the most suitable conditions, in terms of suggestions of chromatographic steps using the orthogonal chromatographic principles, ligands and buffer compositions. The steps can be gradient or isocratic and the gradients can be curved or straight. Using multivariate linear regression responses like resolution of non-resolved peaks or other responses related to purity and recovery are evaluated as function of the descriptors such as conditions from the chromatograms at the points of highest target and highest impurity respectively and the difference in conditions between these points.

The use of inline conditioning for the preparation of buffers in the present method provides control of the buffer and its properties as a function of time or volume along the gradient. More specifically, inline conditioning, also known as IC, is a marketed solution (GE Healthcare) in the bioprocessing area for researchers and process engineers who need to formulate buffer solutions precisely at the time of use, using stock solutions of the buffer components. When using inline conditioning, the storage of prepared buffer is eliminated, thus reducing facility space limitations, and time and effort to transport and maintain buffer containers is reduced.

In one embodiment, the in-line conditioning according to the present invention includes conditioning of a liquid sample to a predetermined pH and/or conductivity before it is loaded to the chromatography column.

The in-line conditioning used according to the present invention may follow the principles and embodiments disclosed in EP 2 269 055 (Björkesten et al). Thus, in one embodiment, the method according to the invention includes determining the relative component proportions of at least one each of: a buffer; an acid or a base; a solvent; and, optionally, a salt, for providing a liquid mixture of pre-defined pH and ionic strength, wherein the relative component proportions are determined using the equation of Debye-Hückel, wherein the ion size parameter a in the Debye-Hückel equation is determined as the weighted mean ion size of all species contributing to the ionic strength of the liquid mixture, and wherein the ionic strength of each species is used as weighting parameter.

In a specific embodiment, the relative component proportions are determined using an iterative procedure. Such an iterative procedure may comprise:
 (a) determining the relative component proportions wherein the pre-defined ionic strength of the liquid mixture is addressed to the species according to a pre-defined distribution among the species;
 (b) on the basis of the relative component proportions determined in the preceding step, calculating the ionic strength of each species in the mixture;
 (c) determining a new set of relative component proportions; taking account of the ionic strength calculated in (b), and
 (d) repeating the steps (b) and (c) until a predetermined convergence criteria is met.

In a specific embodiment, in step (a), the pre-defined ionic strength of the liquid mixture is addressed to the salt species.

In one embodiment of the method according to the invention, the ion size parameter a of the Debye-Hückel equation is determined as $$a = \frac{\sum I_i a_i}{I} \quad (I)$$

wherein $I_i$ is the ionic strength and $a_i$ of species i, and I the total ionic strength.

In a specific embodiment, the ion size parameter a in the Debye-Hückel equation is approximated as $$a = 0.5*(mass)^{1/3} + shell \quad (II)$$

wherein "shell" is fixed at one value for a positively charged species and fixed at a different value for a negatively charged species, In one embodiment, "shell" is fixed at a value in the range of 3.8-4.2, such as 4.0, for positively charged ionic species; and "shell" is fixed at a value in the range of 0-0.2, such as 0, for negatively charged ionic species In an advantageous embodiment, the present invention is used to determine optimized conditions for the chromatographic separation of biomolecules such as proteins, e.g. recombinant proteins or antibodies.

In a specific embodiment, the biomolecule is an antibody, such as a monoclonal antibody, or a fragment or fusion thereof.

In a second aspect, the present invention relates to a system for the determination of chromatography conditions for the separation of a biomolecule, which system comprises
 means for selecting a number of experiments including at least two gradients of two selected quality measures; and
 means for outputting to a controller for carrying out the experiments.

At least two orthogonal quality measure(s) are used, and the selected experiments include in-line conditioning of buffer gradient(s).

The present system may use any or all of the embodiments of the method according to the invention, as described above. In one embodiment, the means for selecting experiments is software capable of predicting a number of experiments representative for the whole range of variables available. Thus, the invention provides a simplification in terms of the number of experiments required to determine efficient conditions for a process wherein a biomolecule is separated. In a specific embodiment, the system according to the invention provides to optimal conditions for chromatographic separation of a specific biomolecule.

In a further aspect, the present invention relates to a computer program for determining chromatographic conditions for the separation of a biomolecule, as described above.

Finally, the present invention also relates to an instrument arranged to determine efficient chromatographic conditions for the separation of a specific biomolecule, which instrument comprises software operating in accordance with the method according to the invention. As the skilled person will appreciate, "comprises" means in this context either as an integral part; or operatively linked to a computer which includes such a program, or software.

DETAILED DESCRIPTION OF THE DRAWINGS

FIG. 1 shows traditional DoE, in accordance with the prior art, with isocratic elution.

Figure 2:
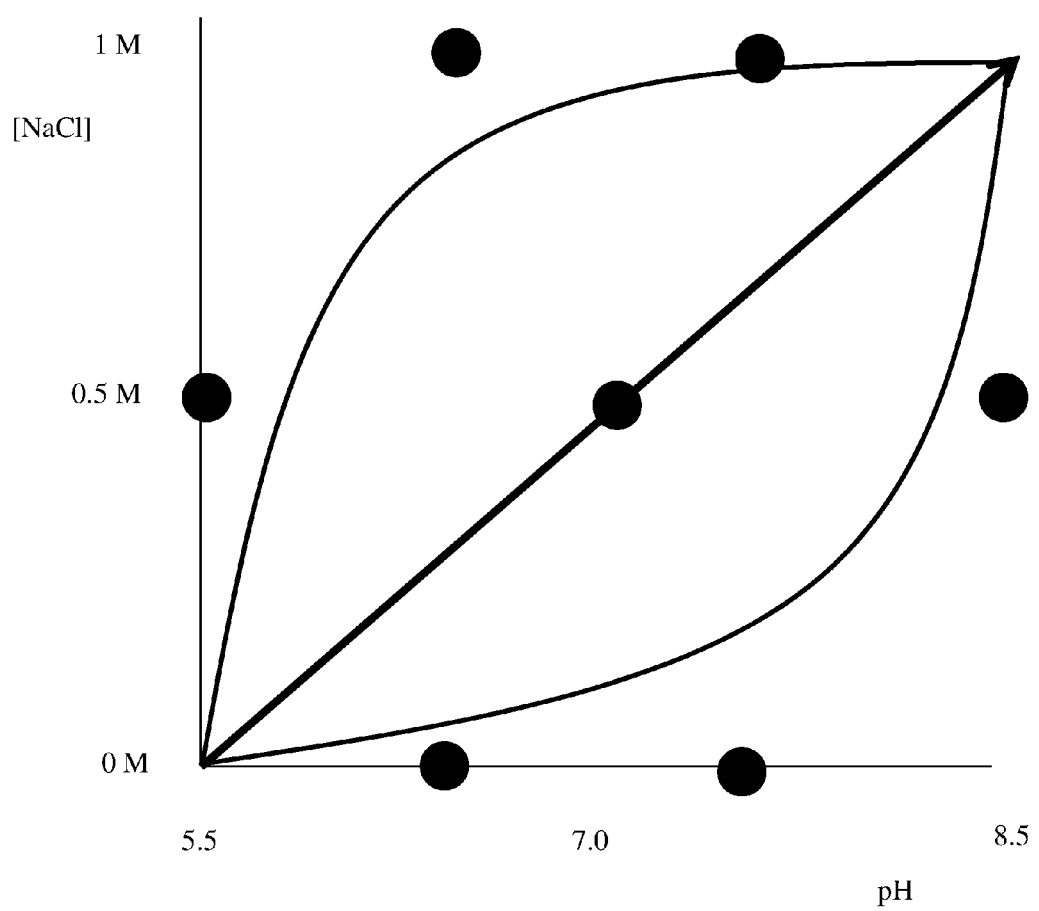
FIG. 2 shows an embodiment of the invention using the orthogonal gradient approach.

FIG. 2 shows an embodiment of the invention using the orthogonal gradient approach. More specifically, one linear and two curved—a concave and a convex—gradients are provided.

EXPERIMENTAL PART

The present examples are provided for illustrative purposes only, and should not be construed as limiting the invention as defined by the appended claims. All references given below and elsewhere in the present application are hereby included herein via reference.

Example 1 (Comparative): Determination of Optimal Conditions for Cation Exchange In order to reduce the number of experiments required to identify optimal conditions for the purification of a recombinant protein using cation exchange chromatography, a traditional Doehlert design (7 chromatographic runs with no replicates) is applied.

A harvest liquid comprising a target recombinant protein is obtained and desalted by gel filtration into the appropriate binding buffer (see below). Purification is performed with HiTrap Capto S 1 ml (GE Healthcare, www.gelifesciences.com), a strong cation exchanger prepacked with BioProcess Capto media for screening and small-scale protein purifications using ion exchange chromatography (IEX).

The experiment is run on an AKTA avant (GE Healthcare, www.gelifesciences.com), which is a preparative chromatography system marketed for development of scalable methods and processes.).

Operating parameters are as follows (CV means column volumes):
Binding buffer: 35 mM NaAc pH 5.5
Equilibration: 5 CV binding buffer
Load: 0.2 CV desalted harvest in binding buffer
Wash: 2 CV binding buffer
Elution: 3 CV <Experimental factor>

The elution fractions are collected requiring 7 analyses to predict the most efficient isocratic conditions for chromatographic separation of the recombinant protein.

Analysis: HPLC SEC (size exclusion chromatography) for concentration of target recombinant protein provides purity and yield for every fraction. The responses are used to train the DoE regression model which then is used to predict the optimal isocratic conditions. Alternatively a qualitative assessment of the elution map may be used to obtain the most suitable conditions.

Example 2: Determination of Conditions According to the Invention

This example uses a simultaneous pH and salt gradient. Three runs (concave, convex and straight) are performed, as illustrated in FIG. 2. The curvature of the gradients is designed so that all the points in the DoE are close to the path of the gradients. In the case of the curved gradients three elution fractions are collected, one for each of the DoE points passed by. In the case of the straight gradient one fraction is collected in the middle of the gradient requiring a total of 7 analyses of purity and yield. The responses are used to train the DoE regression model which then is used to predict the optimal isocratic conditions. Alternatively a qualitative assessment of the elution map may be used to obtain the most suitable conditions.

The invention claimed is:

1. A method for determination of chromatography conditions for separating a biomolecule from a liquid sample, the method comprising,
   a) selecting a number of experiments (N experiments) using design of experiments (DoE);
   b) performing a number of chromatographic runs (M chromatography runs) for said N experiments on a chromatography column with in-line conditioning of at least two gradients of two selected quality measures, wherein paths and curvatures of the gradients are designed so that data points in the DoE are close to the paths of the gradients to obtain N elution fractions during the M chromatography runs, one for each of the DoE points passed by;
   c) analyzing a purity and yield of the N fractions to obtain responses data;
   d) using the responses data to train a DoE regression model; and,
   e) using the DoE regression model to predict isocratic chromatography conditions for said biomolecule;
   wherein the two selected quality measures are orthogonal, and
   wherein the number of chromatography runs (M) is less than the number of experiments of DoE(N).

2. The method according to claim 1, wherein step a) comprises
   i) preliminarily selecting said N experiments using the DoE and
   ii) adjusting experimental parameters of said N experiments to fall on at least two gradients of two selected quality measures.

3. The method according to claim 1, wherein at least one of said at least two gradients is a curved gradient.

4. The method according to claim 1, wherein at least two of said at least two gradients are curved gradients.

5. The method according to claim 1, wherein the quality measures are selected from the group consisting of type of chromatography resin; loading volume, wash volume, elution volume, binding buffer; elution buffer; surface determinants of the biomolecule and impurities present in the liquid sample.

6. The method according to claim 1, wherein the in-line conditioning comprises conditioning of a liquid sample to a predetermined pH and/or conductivity.

7. The method according to claim 6, wherein the conditioning comprising, determining a relative component proportions of at least one each of: a buffer; an acid or a base; a solvent; and optionally, a salt, for providing a liquid mixture of pre-defined pH and ionic strength,
   wherein the relative component proportions are determined using equation of Debye-Hückel,
   wherein an ion size parameter a in the Debye-Hückel equation is determined as a weighted mean ion size of all species contributing to an ionic strength of the liquid mixture, and
   wherein an ionic strength of each species is used as weighting parameter.

8. The method according to claim 7, wherein the relative component proportions are determined using an iterative procedure.

9. The method according to claim 8, wherein the iterative procedure comprises:
   (a) determining the relative component proportions wherein a pre-defined ionic strength of the liquid mixture is addressed to the species according to a pre-defined distribution among the species;
   (b) on the basis of the relative component proportions determined in the preceding step, calculating the ionic strength of each species in the mixture;
   (c) determining a new set of relative component proportions; taking account of the ionic strength calculated in (b), and
   (d) repeating the steps (b) and (c) until a predetermined convergence criteria is met.

10. The method according to claim 9, wherein in step (a), the pre-defined ionic strength of the liquid mixture is addressed to salt species.

11. The method according to claim 7, wherein the ion size parameter a of the Debye-Hückel equation is determined as $$a = \frac{\sum I_i a_i}{I} \quad (I)$$

wherein in equation (I), $I_i$ is the ionic strength and $a_i$ of species i, and I the total ionic strength.

12. The method according to claim 7, wherein the ion size parameter a in the Debye-Hückel equation is approximated as $$a = 0.5*(mass)^{1/3} + shell \quad (II)$$

wherein in equation (II), the parameter "shell" is fixed at one value for a positively charged species; and at a different value for a negatively charged species.

13. The method of claim 12, wherein in equation (II), the parameter "shell" is fixed at a value in a range of 3.8-4.2 for positively charged ionic species and at a value in a range of 0-0.2 for negatively charged ionic species.

14. The method according to claim 1, wherein the DoE includes multivariate analysis.

15. The method according to claim 1, wherein the biomolecule is an antibody.

16. An apparatus for determining isocratic chromatography conditions for separating a biomolecule from a liquid sample, the apparatus comprising,
a computer configured to communicate with a software to execute a set of instructions to:
a) select a number of experiments (/V experiments) using design of experiments (DoE);
b) output to a controller for carrying out a number of 44 chromatography runs (M chromatography runs) for said N experiments on a chromatography column with in-line conditioning of at least two buffer gradients of two selected quality measures wherein paths and curvatures of the gradients are designed so that the points in the DoE are close to the paths of the gradients to obtain N elution fractions during the M chromatography runs, one for each of the DoE points passed by;
c) analyze a purity and yield of the N elution fractions to obtain responses data;
d) use the responses data to train a DoE regression model; and
e) use the DoE regression model to predict isocratic chromatography conditions for said biomolecule based on the results from b);
wherein the two selected quality measures are selected from the group consisting of type of chromatography resin; loading volume, wash volume, elution volume, binding buffer; elution buffer; surface determinants of the biomolecule and impurities present in the liquid sample and are orthogonal to each other, and
wherein the number of chromatography runs (M) is less than the number of experiments of DoE (N).

17. The apparatus according to claim 16, wherein the means for selecting experiments is software capable of predicting a reduced but representative number of experiments, preferably by using DoE.

18. The apparatus according to claim 16, which is an instrument comprising software and optionally a robot for performing all or part of a method.

19. A method for determination of chromatography conditions for separating a biomolecule from a liquid sample, the method comprising, a1) preliminarily selecting a number of DOE experiments (N DoE experiments) using multivariate analysis,
a2) adjusting experimental parameters of said experiments to fall on at least two gradients of two selected quality measures,
b) performing a number of chromatography runs (M chromatography runs) for said N experiments on a chromatography column with in-line conditioning of at least two gradients of two selected quality measures wherein paths and curvatures of the gradients are designed so that the points in the DoE are close to the paths of the gradients to obtain N elution fractions during the M chromatography runs, one for each of the DoE points passed by;
c) analyzing a purity and yield of the N elution fractions to obtain responses data;
d) using the responses data to train a DoE regression model; and,
e) using the DoE regression model to predict isocratic chromatography conditions for said biomolecule;
wherein the two selected quality measures selected from the group consisting of type of chromatography resin; loading volume, wash volume, elution volume, binding buffer; elution buffer; surface determinants of the biomolecule and impurities present in the liquid sample and are orthogonal to each other,
wherein at least two of said at least two gradients are curved gradients, wherein the number of chromatography runs (M) is less than the number of experiments of DoE (N),
wherein the in-line conditioning comprises conditioning of a liquid sample to a predetermined pH and/or conductivity, and
wherein the biomolecule is a monoclonal antibody, or a fragment or fusion.

20. The method according to claim 19, wherein the conditioning comprising determining the relative component proportions of at least one each of: a buffer; an acid or a base; a solvent; and, optionally, a salt, for providing a liquid mixture of pre-defined pH and ionic strength,
wherein the relative component proportions are determined using the equation of Debye-Hückel,
wherein the ion size parameter a in the Debye-Hückel equation is approximated as $$a = 0.5*(mass)^{1/3} + shell \quad (II)$$

wherein in equation (II), the parameter "shell" is fixed at a value in the range of 3.8-4.2 for positively charged ionic species; and at a value in the range of 0-0.2 for negatively charged ionic species, and
wherein the ionic strength of each species is used as weighting parameter;
wherein the relative component proportions are determined using an iterative procedure, comprising:
(a) determining the relative component proportions wherein the pre-defined ionic strength of the liquid mixture is addressed to the species according to a pre-defined distribution among the species, wherein the pre-defined ionic strength of the liquid mixture is addressed to the salt species;
(b) on the basis of the relative component proportions determined in the preceding step, calculating the ionic strength of each species in the mixture;
(c) determining a new set of relative component proportions; taking account of the ionic strength calculated in (b), and (d) repeating the steps (b) and (c) until a predetermined convergence criteria is met.

* * * * *